(12) United States Patent
Ward et al.

(10) Patent No.: US 8,888,829 B2
(45) Date of Patent: Nov. 18, 2014

(54) HAND HELD SYSTEM FOR ANTIFUNGAL TREATMENT

(71) Applicants: Anthony Robert Ward, Greenfield, IN (US); Thomas Owen Ward, Greenwood, IN (US); Zachary McBride, Kalamazoo, MI (US)

(72) Inventors: Anthony Robert Ward, Greenfield, IN (US); Thomas Owen Ward, Greenwood, IN (US); Zachary McBride, Kalamazoo, MI (US)

(*) Notice: Subject to any disclaimer, the term of this patent is extended or adjusted under 35 U.S.C. 154(b) by 0 days.

(21) Appl. No.: 13/766,577

(22) Filed: Feb. 13, 2013

(65) Prior Publication Data
US 2013/0211481 A1    Aug. 15, 2013

Related U.S. Application Data

(60) Provisional application No. 61/598,838, filed on Feb. 14, 2012.

(51) Int. Cl.
*A61N 5/06*    (2006.01)

(52) U.S. Cl.
CPC ....... *A61N 5/0624* (2013.01); *A61N 2005/0662* (2013.01); *A61N 2005/0644* (2013.01); *A61N 2005/0667* (2013.01)
USPC ................................. 607/88; 607/95; 606/10

(58) Field of Classification Search
CPC .................................. A61N 5/06; A61B 18/20
See application file for complete search history.

(56) References Cited

U.S. PATENT DOCUMENTS

| | | | | |
|---|---|---|---|---|
| 4,389,085 A | * | 6/1983 | Mori | 359/591 |
| 4,717,227 A | * | 1/1988 | Mori | 126/571 |
| 5,116,329 A | * | 5/1992 | Vannus et al. | 606/11 |
| 5,885,211 A | * | 3/1999 | Eppstein et al. | 600/309 |

* cited by examiner

*Primary Examiner* — Lynsey Crandall
(74) *Attorney, Agent, or Firm* — Brinks Gilson & Lione

(57) ABSTRACT

An antifungal treatment system includes a light source. The light source may be positioned in a housing having an exit aperture. The light source may be energized to generate a concentrated beam of electromagnetic radiation. The electromagnetic radiation may be visible light radiation that includes infrared radiation. When energized, the concentrated beam may be directed out of the exit aperture by the light source. A focal point of the concentrated beam may be provided in a target area external to the housing to penetrate a human nail and destroy fungus resident thereunder.

19 Claims, 13 Drawing Sheets

LASELOGIX

Please select an option:

[ Start My Treatment ]

[ Review Treatment ]

[ About Product ]

FIG. 6

HAND HELD SYSTEM FOR ANTIFUNGAL TREATMENT

This application claims the benefit of priority of U.S. Provisional Patent Application No. 61/598,838, filed Feb. 14, 2012, which is incorporated herein by reference in its entirety.

BACKGROUND OF THE INVENTION

1. Technical Field

This invention relates to antifungal treatments and more specifically to a hand held system for treating fungus.

2. Related Art

Many people suffer from nail infections caused by fungus. Despite years of trying, several medical solutions are unable or only partially effective in successfully treating such nail infections. Possible solutions include laser treatment, prescription drugs and topical medications; however, these types of treatment are expensive, and sometimes ineffective.

SUMMARY

A hand held antifungal treatment system for antifungal treatment is a low-to-moderate cost system that may be used to kill fungal nail infections (Onychomycosis). The system includes a light source to generate visible light that can be directed at the infected area. The light source is capable of generating a concentrated beam of light capable of illuminating and heating a target area. The beam of light may be in a range of the electromagnetic spectrum between about 100 nanometers and 1200 nanometers that includes infrared radiation. In one example, the light source may be a solar powered light source operated with a wavelength less than about 760 nanometers. In another example, the light source may be a laser, with a wavelength between 400 and 1200 nanometers.

The system is designed for home use by consumers. In one example, the system may be a low powered system, which can be placed in proximity to a part of a user's body containing a nail, such as toes or fingers. The system may, for example, be attached onto the user's body, such as a user's toes at night, during the day at work, or while watching television. The system may, for example, be a hand-held device which the user interacts with to document and treat their fungal nail infection. The system may operate in an automated fashion to perform a predetermined treatment sequence upon the system being initiated by the user. Alternatively or in addition, the system could be initiated by the user, and/or manually manipulated by the user. The user can direct the treatment manually. In some examples, the treatment may be user directed by manipulating/controlling the light source. In other examples, the treatment may be user directed using a touch-display GUI, push-buttons, or peripheral switches, or any combination of the above.

The treatment sequence may include a sequence of one or more stages. In one stage, the system may subject a predetermined area of the user to the output of one or more light sources for a predetermined period of time. The light source(s) may be movable or stationary. The user may direct the system to the area being treated by way of an inspection system, such as a camera with infrared capabilities, which can detect where the infrared energy is striking the infected area since the infrared energy is invisible to the human eye. In the example of the camera, the user may also view the results of the treatment through a display. The display may be part of the system, or may be a separate display in communication with the system. The inspection system may also be used to document the current state of the user's fungal nail infection.

The system may also include a topical application stage in which one or more solutions are applied to the area. One solution may be a temperature-sensitive, adhesive liquid bandage. The solutions may be collected to form a bath or other liquid reservoir such that the part of the user's body is immersed. Alternatively, a brush, shower, mist, or some other form of intermittent application may be used. The system may also include a mechanical clipping or grinding stage.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention may be better understood with reference to the following drawings and description. The components in the figures are not necessarily to scale and the components illustrated are not intended to provide proportionality between respective features, emphasis instead being placed upon illustrating the principles of the invention. Moreover, in the figures, like referenced numerals designate corresponding parts throughout the different views.

FIG. 6 is an example of an antifungal treatment system Graphical User Interface (GUI).

DETAILED DESCRIPTION OF THE PREFERRED EMBODIMENTS

Figure 1:
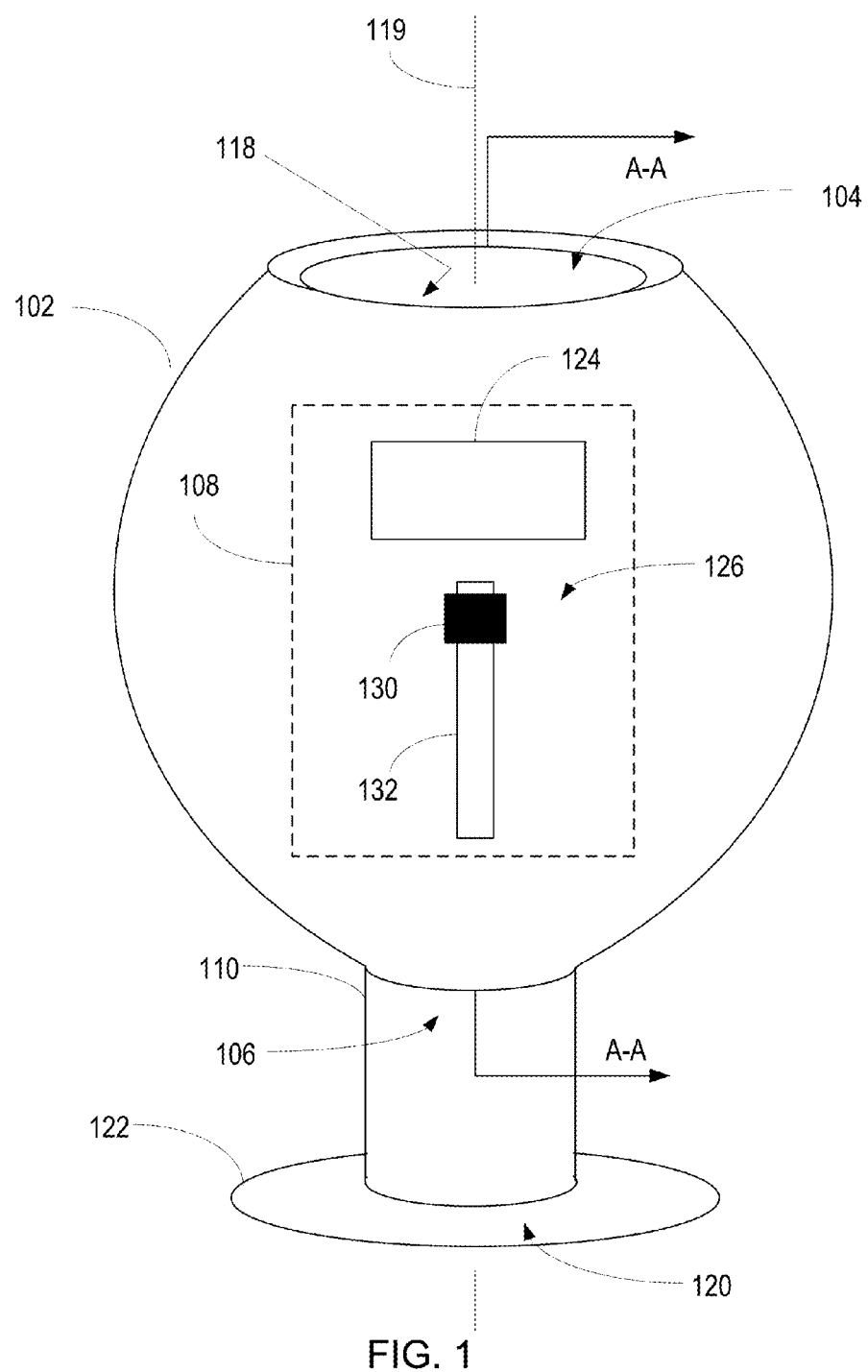
FIG. 1 is a perspective view of an example antifungal treatment system.

The antifungal treatment system may include at least one light source and a user interface. In other examples, the antifungal treatment system may also, or optionally, include a processor, a power supply, and an inspection system, such as a camera with or without infrared capabilities. The user interface may be any form or device or system that allows a user to interact with the system. In one example, the user interface may include visual indicators, such as lights, positional devices, or any other device or mechanism capable of toggling between two or more visually different states. The user interface may also include one or more tactile devices, such as switches, buttons, or sliders, and/or one or more audio indicators, capable of toggling between one or more states. In one example, the system may include a graphical user interface (GUI) and a display, such as an LCD display, which supports the GUI, push-button events, touch events, remote control capabilities, and/or a voice command capability.

The light source may be any device(s) capable of emitting electromagnetic radiation in the form of light energy that include visible white light and infrared radiation. In one example, the system may include a light source generating visible white light using solar energy. In another example, any other source of electrical power may be used by the light source to generate light energy. In still other examples, the light source may include multiple light sources, such as a visible light source and an infrared light source. With light sources energized by electrical power, light sources such as high intensity light bulbs, a laser, or any other source capable of emitting visible white light that includes infrared radiation may be used. In one example, the light source may generate electromagnetic radiation from an external light source, such as solar light energy, in which the ultraviolet portion of the solar light energy has been omitted. In another example, the light energy may be generated as ultraviolet-C (UVC) energy in a range of about 400 nanometers to about 1200 nanometers of light. The light energy may be provided such that localized light energy in a target area neutralizes biological organisms, such as bacteria, and fungus.

Example external light sources include solar power generated by the sun, or any other source of visible light that includes infrared radiation. As used herein, the terms "solar" and "solar power" and "solar energy" should be construed to include not only visible light energy produced by the sun, but also any other source of visible light energy generated independently and external to the antifungal treatment system 100.

Such external light sources may be used by the system to generate electrical energy from solar power supplies such as photovoltaic cells providing electrical energy to a powered light source included in the system. Alternatively, or in addition, such external light sources may be used directly by the light source included in the system to generate electromagnetic energy that is visible light including infrared radiation. An example light source in the system that may directly use light energy from external lights sources is a convex lens that is thicker in cross-section toward a middle portion and thinner in cross section toward a peripheral edge of the lens. Example powered light sources includes a low-pressure mercury type, a cold cathode type, or a light emitting diode (LED) type light source. In some examples, solar powered light sources included in the system may receive solar energy, which can be concentrated to form a light beam that can be directed to a target area. Light sources, such as a laser, powered from an electric power supply may be continuously operated with an operational wattage, such as about one to about six watts alternating current, or potentially even greater operational wattages, such as up to 10 watts or greater. The light source may be removable from the antifungal treatment system to allow user replacement and/or maintenance. Electric powered light sources may operate in a pulsed fashion, with an adjustable frequency or duty cycle. An example of an adjustable frequency and duty cycle of a light source is 1 Hertz at 75% duty cycle.

Where the light source has a variable light energy output, the appropriate level of light energy of the light source may be determined by application of various levels of light energy to a culture of one or more forms of fungus, such as common forms of toenail or nail fungus to identify the appropriate intensity and duration that is needed to neutralize biological organisms. The light energy may be emitted through toenail clippings to simulate a natural setting. Alternatively, or in addition, the user may determine the light energy output level and duration based on sensing the effect of the light energy in the target area. For example, the user may sense heat or light intensity and adjust the magnitude of the light energy output and duration accordingly. In some examples, temperature sensors, light energy sensors, cameras, or any other form of sensing device may be used in a control loop to modulate the light energy output of the light source.

FIG. 1 shows an example of an antifungal treatment system 100. The antifungal treatment system 100 includes a housing 102. The housing may optionally include a first aperture 104, or entry aperture. In addition, the housing 102 includes a second aperture 106, or exit aperture. As optional features, the antifungal treatment system 100 may also include a user interface 108, and an alignment tool 110. In other examples, any other of the features and/or functionality described herein may be included in the antifungal treatment system 100 illustrated in FIG. 1. In other example embodiments, the can include a single magnifying convex lens and a single aperture.

The housing 102 may be formed of any rigid material, such as plastic or metal and include an interior cavity or chamber 118. The first aperture 104 and second aperture 106 may provide access to the interior chamber 118. In addition, or alternatively, the housing 102 may have an access panel, or may be include two or more separable portions to allow access to the interior cavity or chamber 118. In FIG. 1, the housing 102 is illustrated as generally ellipsoid, or egg-shaped, however, in other examples, the housing 102 may be spherical, cylindrical, cuboid, hexahedron, tetrahedron, or any other shape that defines an interior chamber 118 and includes a longitudinal central axis 119.

In addition, or alternatively, to providing access to the interior chamber 118, the entry aperture 104 may allow for entry of visible light energy from an external light source, such as sunlight from the sun. Thus, in some examples, photovoltaic cells or any other mechanism for converting solar light energy to electric energy may be disposed in the interior chamber 118 to receive solar energy through the entry aperture 104. Alternatively, or in addition, the entry aperture 104 may provide an alignment function by providing a visual path through the housing 102 to the exit aperture 106 so that a user may view, via the entry aperture 104, objects external to the housing 102 and adjacent to the exit aperture 106.

The exit aperture 106 may provide an exit point for light energy emitted by a light source included in the housing 102. The exit aperture 106 may optionally be surrounded by the alignment tool 110. In FIG. 1, the alignment tool 110 is formed as a cylinder having an interior cavity and is coupled with the housing 102, such as an outer surface of the housing 102. In other examples, the alignment tool 110 may be a contiguous structure formed in any other shape, or may be formed of a number of connected members. The alignment tool 110 is formed to surround the exit aperture 106, and extend away from the outer surface of the housing 102 to form an alignment aperture 120. Thus, in the example where the alignment tool 110 is formed of longitudinally connecting members, struts may extend from the housing 102 to a circular, square, elliptical (or any other shaped) member formed to define the alignment aperture 120.

The alignment tool 110 may be fixedly coupled with the housing 102 such that the alignment aperture 120 is maintained at a predetermined distance from the housing 102.

Alternatively, the alignment tool 110 may be movably coupled with the housing 102 such that the alignment aperture 120 may be selectively positioned at varying distances from the housing 102. In one example, the alignment tool 110 may retract and extend from the housing 102 such that the alignment aperture 120 may be moved to a position to optimize the concentration of visible light energy in a target area.

The antifungal treatment system 100 may also include a shroud 122. The shroud 122 may be a translucent material designed to filter or otherwise protect the eyes of a user from the intensity of visible light of the electromagnetic radiation present in the target area. The material of the shroud 122 may be any material capable of reducing glare and bright light such as materials similar to those used in sunglasses. In FIG. 1, the shroud 122 is coupled with the alignment tool 110 to operate as a curtain between an eye of a user observing the target area and the electromagnetic radiation being provided as visible light in the target area. In other examples, alternatively, or in addition, the shroud 122 may be coupled with the housing 122. In still other examples, the alignment tool 110 may be formed to include translucent material positioned to operate as a shroud and allow visibility of the target area through the translucent material. In addition, or alternatively, the shroud 122 may be a separate article, that may be, for example worn by the user.

In addition, the system may include an orientation sensor, such as a gyroscope or a level sensor, capable of measuring pitch and roll of the housing 102 with respect to a transverse surface, such as the ground. The orientation sensor may sense the alignment of the system such that the light source 202 may only be energized when the longitudinal axis 119 of the housing 102 is oriented in a predetermined range of positions, or an area, where the housing 102 is substantially vertical. For example, the level sensor may enable energization of the light source 202 only when the longitudinal axis 119 of the housing 102 is positioned within a predetermined range of being substantially vertical, such as within +/−twenty degrees of parallel to a vertical axis. Thus, the range of motion of the longitudinal axis 119 of the housing 102 creates a predetermined area defined as frusto-conical in which the housing 102 may be oriented to enable energization of the light source. In other words, if the longitudinal axis 119 of the housing 102 is adjusted to be more than a predetermined distance, such as twenty degrees from perpendicular to a transverse surface, such as the ground, the light source may be deenergized. Accordingly, for example, the light source may be deenergized by the orientation sensor whenever the longitudinal axis 119 of the housing 102 is outside the predetermined area defined by the frusto-conical shape such that the concentrated beam of the light source is directed towards a target area in a plane that is more than a predetermined angle away from parallel with a transverse surface. Thus, for example, the system may denergize the light source, when the focused concentrated beam of light generated by the light source is directed anywhere other than substantially towards the ground.

The user interface 108 may provide information regarding operation of the antifungal treatment system 100 and/or user control of the antifungal treatment system 100. In FIG. 1, the user interface 108 includes a control panel 124 and a light source control 126. In other examples, any other devices or mechanism can be included to control and provide information regarding operation of the antifungal treatment system 100. The control panel 124 may include a display, such as an LCD or LED display. In one example, the display may provide operational information such as timing information regarding operation of the light source in the target area. In addition, or alternatively, alignment information regarding the light energy emitted from the housing 102 through the exit aperture 106 may be provided. The light source control 126 may provide capability to enable and disable the emission of light energy by the light source. In FIG. 1, the light source control 126 is in the form of a multi-position switch 130 disposed in a slot 132 formed in the housing 102, however, in other examples, any other form of control or mechanism may be used.

Figure 2:
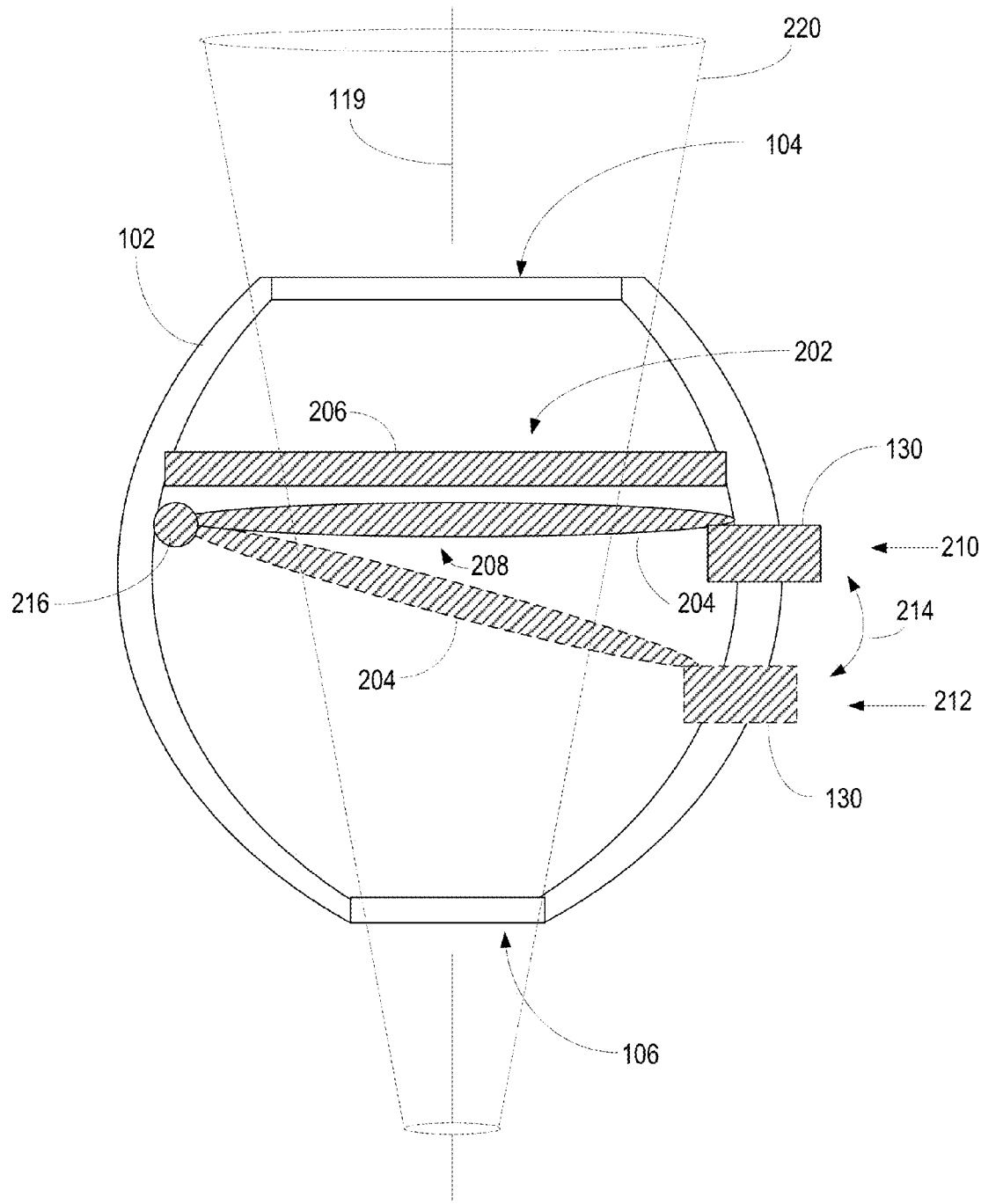
FIG. 2 is a cut-away of the example antifungal treatment system of FIG. 1.

FIG. 2 is an example cut-away of the antifungal treatment system 100 of FIG. 1 along lines A-A in FIG. 1. In the example of FIG. 2, a light source 202 is illustrated as positioned in the interior chamber 118 of the housing 102. The light source 202 of this example is a solar light source that includes a convex lens 204. Optionally, the light source 202 of this example solar light source may also include a filter 206. In other examples, the light source 202 may be a powered light source such as a light bulb, a laser or any other source of electromagnetic radiation in the form of visible light that includes infrared radiation.

The lens 204 may be round, square, or any other shape, and may form a generally planar member having a top surface and a bottom surface that extend to an outer peripheral edge. The lens 204 may be directly or indirectly, moveably, or fixedly coupled with an inner wall of the housing 102. The lens 204 may include a central region 208 and surrounding peripheral region. The lens 204 may be convex at both the top surface and the bottom surface such that the cross-section thickness proximate the central region 208 is greater than the cross-sectional thickness within the peripheral region.

In FIG. 2, the light source control 126 includes the switch 130, which is selectively positioned to hold the lens 204 in a first predetermined position 210 to enable energization of the light source 202, and hold the lens in a second predetermined position 212 to disable energization of the light source 202. In this example, the switch 130 supports a portion of the peripheral edge of the lens 204 proximate the switch 130 such that as the switch 130 is toggled between the first and second positions 210 and 212, as illustrated by the arrow 214, the lens 204 corresponding changes position as illustrated by the dotted outline of the lens 204 in FIG. 2. The light source control 126 includes a pivot point 216 that movable couples the lens 204 to an inner wall of the housing 102 at a distal peripheral edge of the lens 204 opposite the switch 130 to enable the lens 204 to be moveable between the first and second positions 210 and 212.

The filter 206 (if included) may be fixedly positioned in the housing 102 adjacent the lens 204. The filter 206 may allow a portion of electromagnetic radiation to pass, while blocking a predetermined frequency range, such as the frequency range of ultraviolet light that may be present in the light energy. The filter 206 may be positioned anywhere in the housing 102 to perform this function. In FIG. 2, the filter 206 is positioned to filter light energy prior to receipt of the light energy by the lens 204.

During operation in the example of a solar powered light source being included in the antifungal treatment system 100 illustrated in FIGS. 1 and 2, solar energy provided by an external light source, such as the sun, may be received in the entry aperture 104 as visible light. The solar energy may pass through the filter 206 to the lens 204 as filtered solar energy in the form of visible light that includes infrared radiation. The lens 204, may generate electromagnetic energy from the filtered solar energy in the form of a concentrate beam of light energy. Where the antifungal treatment system 100 includes the light source control 126 illustrated in FIG. 2, when the lens 204 is in the first predetermined position 210, the electromagnetic energy generated by the lens 204 may be emitted from the exit aperture 106.

Generation of electromagnetic energy by the lens 204 may be based on the alignment of the housing with respect to the external light source, such as the sun so that the solar energy strikes substantially the entirety of the lens 204. In other words, the rays (or vectors) representing the solar energy are aligned to enter the entry aperture 104 so as to strike the convex surface of the lens 204 substantially perpendicular to the convex surface. In this regard, the lens 204 may be positioned a predetermined distance from the entry aperture 104 such that the rays of the solar energy are partially or completely blocked from the convex surface of the lens 204 when the housing is mis-aligned with respect to the external light source. Alternatively, or in addition, a light pipe, mirrors, or any other directional control mechanism may be used to direct the solar energy to be incident substantially perpendicular on the convex surface of the lens 204.

Upon the solar energy striking the convex surface of the lens 204 substantially perpendicular to the convex surface, the lens operates to concentrate and focus the solar energy to generate the electromagnetic energy as a focused beam having a focal point outside the housing 102. Due to the position of the lens 202, the light source is energized, and the focused beam, concentrated beam, is emitted from the housing 202 via the exit aperture 106. Thus, the electromagnetic energy generated by the lens 204 may be concentrated energy in the form of a focused beam or concentrated beam having a focal point external to the housing 102. In the example of FIG. 2, when the switch 130, and correspondingly the lens 204 are in the second predetermined position 212, the alignment of the lens 204 within the housing 102 is such that the rays of solar energy are unable to strike the lens 204 substantially perpendicular to the convex surface. Accordingly, the focused beam is not formed. Alternatively, or in addition, due to the position of the lens 204 in the second predetermined position 212, any electromagnetic energy generated by the lens 204 from the solar energy is not directed out of the exit aperture 106. Accordingly, in the example of FIG. 2, when the switch 130 is in the second predetermined position 212, the light source 202 is deenergized.

In other examples configurations similar to FIG. 2, the light source power control 126 may be omitted, and the lens 204 may be maintained in a fixed position. In this example configuration, positioning of the housing 102 provides energization and deenergization of the lights source. Thus, when the longitudinal axis 119 of the housing 102 is positioned such that the solar energy is incident on the lens 204, the light source 202 is energized, and electromagnetic energy is generated. On the other hand, when the housing 102 is otherwise positioned, the light source 202 is deenergized since insufficient solar energy enters the entry aperture 104 and strikes the lens 204 at the proper angle to generate electromagnetic energy. Thus, in this example, the housing 102 itself operates as an orientation sensor to deenergize the light source 202 when the housing 102 is oriented such that the solar energy does not strike the lens 204 at the correct predetermined angle, or not at all, due to the obstruction of solar energy by the housing 102. Accordingly, when the longitudinal axis 119 of the housing 102 is positioned outside the predetermined area define by a frustoconical shape 220 with respect to a transverse surface, the light source 202 may be deenergized.

In other examples, where the light source 202 is a powered light source, the switch 130 may be an electrical switch capable of interrupting the supply of power to the light source 202. Alternatively, or in addition, the light source control 126 may include one or more shutters or other mechanical devices cable of blocking the light path through the housing such that the solar energy does not reach the light source 202, and/or the electromagnetic energy generated by the light source 202 is prevented from being emitted from the housing 102.

In still other examples, a transparent material, such as glass, plastic, or some other material that allows the visible light and infrared light to pass through may be disposed in the entry aperture 104 and/or the exit aperture 106. The transparent material may be formed as a planar surface having a first side facing into the interior cavity 118, and a second side facing away from the housing 102. The transparent material may span the entry aperture 104 and/or the exit aperture 106 to provide a protective function to keep debris such as dust and foreign objects out of the interior cavity 118. The transparent material may also, for example, provide light blocking functionality by including the capability to transition to a darkened or otherwise opaque state in order to deenergize the light source by blocking the light path. For example, the transparent material may be electrochromic glass, suspended particle glass, or liquid crystal glass that darkens when subject to electric current. The transparent material may be powered from a power supply, a battery, an external light source, solar power, or by any other source of current, and may be controlled with the light source control or a separate control. The transparent material and corresponding current controller may be solid state and operation of the dimming feature may be in accordance with a timer, a sensing device, or any other mechanism, as described herein, to energize and deenergize the light source. Further, selective variable darkening of the transparent material may be used to control the intensity of the concentrated beam of light by varying the degree of darkening in accordance with a desired energy level or intensity of the concentrated beam of light being provided from the exit aperture 106. Such a variable darkening control may be based on temperature, light intensity, length of exposure of a user in the target area, angle of incidence of solar rays, or any other parameters associated with the energy level of the concentrated beam. In addition, or alternatively, the transparent material may include the previously discussed filter capability used to filter UV light.

Indication of energization and deenergization of the antifungal treatment system 100 may be provided by the control panel 124. For example, an indicator light may be provided that is illuminated when the light source 202 is energized. In one example, the indicator light may be electrically powered by electricity from a power supply or solar power. Alternatively, the indicator light may be illuminated directly by either or both of the solar power and/or the electromagnetic power generated by the light source 202.

In one example using an external light source, such as the sun, for solar power, mirrors may be strategically positioned in the interior cavity of the housing 102 such that the indicator is illuminated when solar power rays are incident on the light source 202 such that electromagnetic power is generated. For example, the indicator may indicate when the light rays are incident on the photovoltaic cells or the lens 204. In this example configuration, the indicator light may be used by a user to align the housing 102 with respect to the external light source, such as the sun, such that the electromagnetic energy is generated. In addition or alternatively, the indicator light of this example may provide the user a power output level indication of the electromagnetic energy generated by the light source by positioning the indicator light, filters, and/or reflective surfaces in the housing such that light intensity of the indicator varies as the housing 102 is manipulated with respect to the external light source. Alternatively, or in addition, multiple indicator lights may be included such that illumination of more or less indicator lights and/or intensity of such illumination provides an indication of power level of the output electromagnetic energy.

Where the alignment tool 110 is included in the antifungal treatment system 100, the concentrated beam may be aligned and focused in a target area that is identified using the alignment aperture 120. The alignment tool 110 may focus the concentrated beam by providing a focus location and a focus distance from the housing 102. The focus distance may be adjusted by extending and retracting the alignment tool 110 with respect to the housing 102. The focus location may define the target location in which an object such as a finger or toe should be positioned to intercept the electromagnetic energy generated by the light source 202. In FIG. 2, the alignment aperture 120 may be a predetermined size, such as a predetermined diameter to define the target area such that an object positioned in contact with a surface of the alignment tool 110 facing away from and distal to the housing 102, is positioned in the target area.

Figure 3:
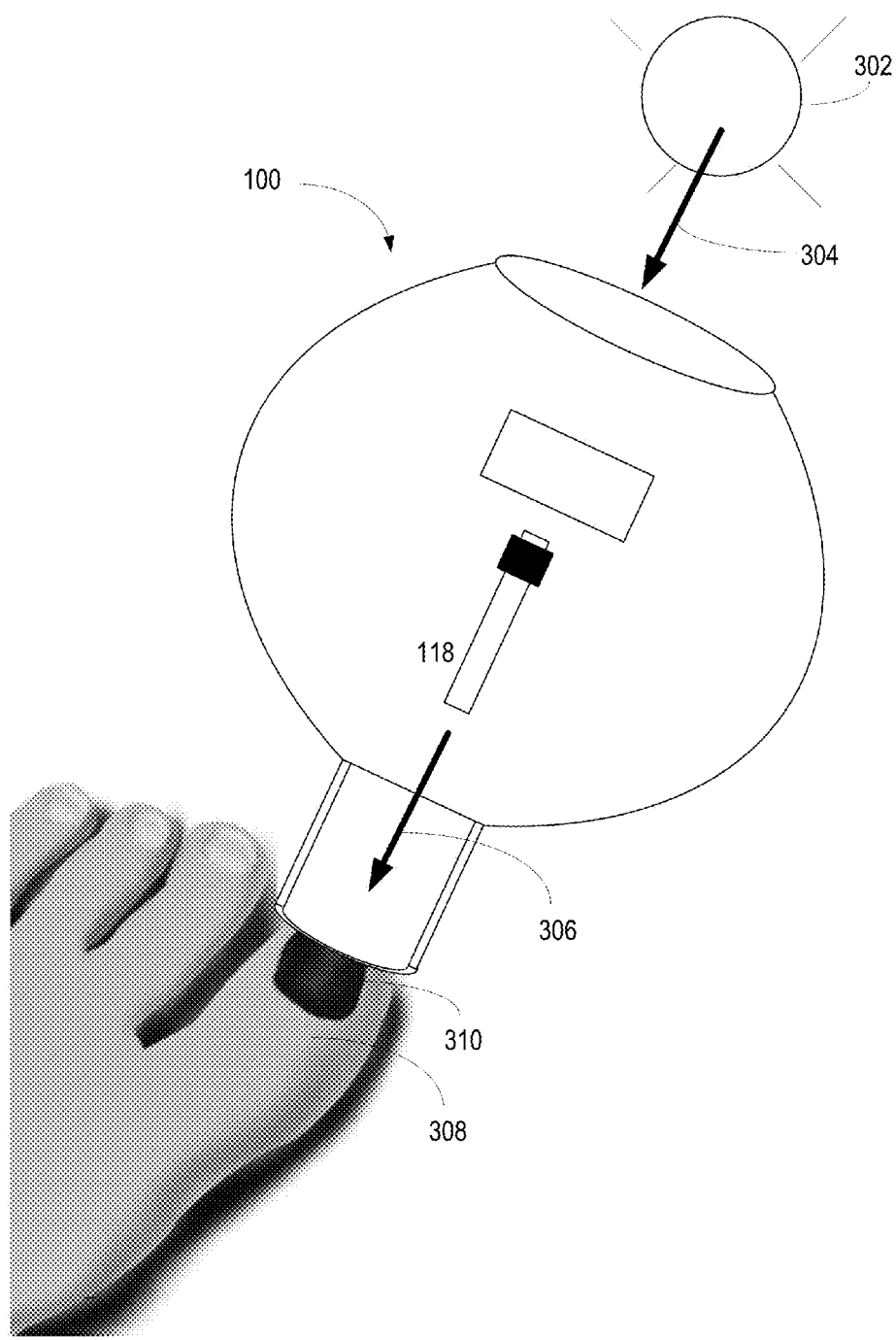
FIG. 3 is example operation of the antifungal treatment system of FIGS. 1 and 2.

FIG. 3 is an example use of the antifungal treatment system 100 of FIGS. 1 and 2 in which an external light source 302, which is the sun, is used to supply solar energy rays 304 to the antifungal treatment system 100. The longitudinal axis 119 of the housing 102 may be aligned with the solar energy rays 304. Once the light source is energized by positioning the housing 102 to align the longitudinal axis of the housing 102 within the predetermined area defined by the frusto-conical shape 220, (FIG. 2) the antifungal treatment system 100 outputs electromagnetic radiation 306. In this example, a toe 308 of a user is positioned in the alignment tool 110 so that the concentrated beam is positioned on the target area, which is this case is a toenail 310 of the toe 308.

In some examples, the antifungal treatment system 100 may be controlled mechanically. In other examples, the antifungal treatment system 100 may include automated features controlled with a processor to direct operation of the antifungal treatment system 100. The processor and any other control related features (either mechanical or electrical) may be included the control panel 124.

Referring to FIGS. 1-3, a feature that may be included in the antifungal treatment system 100 may be a timer. The timer may be a standalone timer, or may be part of another device, such as a processor. The timer may be used in connection with operation of the light source 202 on a target area. For example, a user may be kept appraised of the length of time the light source 202 is supplying electromagnetic radiation to a target area. In another example, the timer may be used to energize and deenergize the light source after a predetermined period of time. Alternatively, or in addition, the timer may provide an indication of when a new target area should be selected, or may provide any other time based functionality.

Another feature of the antifungal treatment system 100 may include automated determination of the focal point using a processor. In this example configuration, adjustment of the alignment tool 110 may be automated such that a length of extension away from the housing 102 of the alignment tool 110 may be automatically adjusted to optimize the focal point of the focused beam in the target area. Alternatively, or in addition, the length of time the object in the target area is exposed to the concentrated beam may be automated to avoid erroneous lengths of exposure. Control of the alignment tool and exposure time may be based on a feedback loop operated by the processor using a sensor such as a temperature sensor or a camera and predetermined corresponding setpoint parameters. In addition, any of the features and functionality described herein, automated or mechanical, may be included in the antifungal treatment system 100 described and discussed with respect to FIGS. 1-3.

Figure 4:
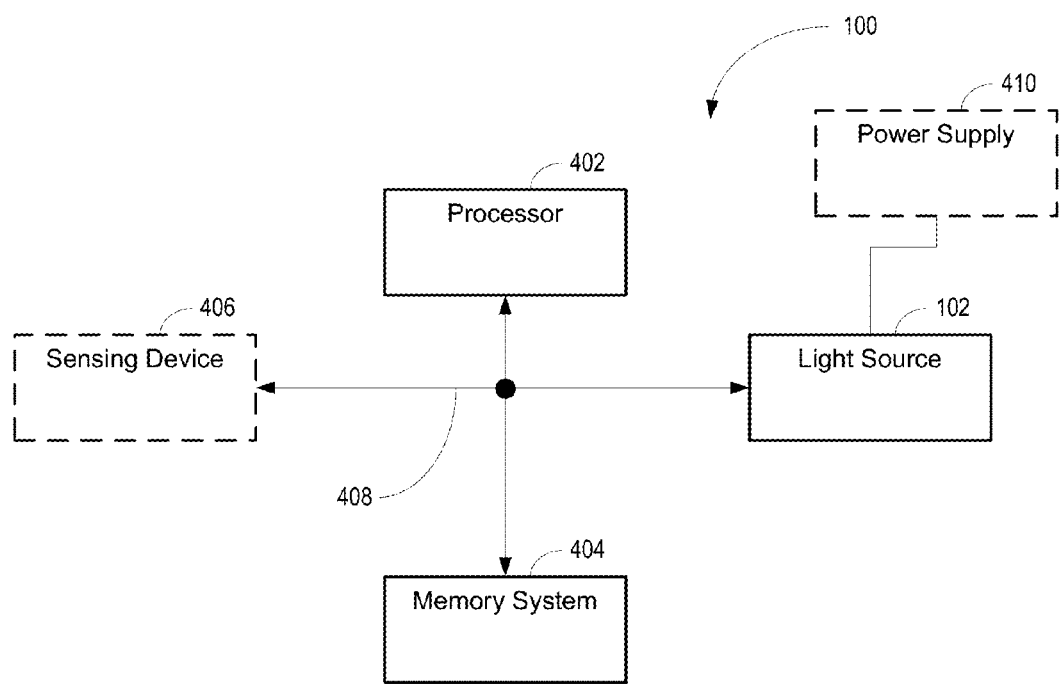
FIG. 4 is a block diagram of an example of an antifungal treatment system.

FIG. 4 is an example of a computer based antifungal treatment system 100. The system may include the light source 102, a processing unit 402, and a memory system 404. In some examples, the system 100 may also include a sensing device 406. The sensing device 406 may be used in control of the antifungal treatment system 100 with the processor 402. For example, when the light source 102 is a laser, the sensing device 406 may be used by the processor 402 to automatically modulate the frequency and duty cycle of the laser. In this configuration, the surface temperature and light intensity at the point of application (the target area) may also be monitored by the system. In this configuration, the dehydration of the culture may be monitored. Additionally, the configuration can monitor the reproduction of low versus high infrared light and low versus high visible light. The system is not limited to any computing device which can provide the functionality herein described. The sensing device may be a camera, such as a CCD camera can take JPEG images. The processor 402 can store or transmit these JPEG images for the user. The computer based system can include memory in the memory system 404 to store all data.

The processor 402 may be any form of device(s) or mechanism(s) capable of performing logic operations, such as a central processing unit (CPU), a graphics processing unit (GPU), and/or a digital signal processor (DSP), or some combination of different or the same processors. The processor 402 may be a component in a variety of systems. For example, the processor 402 may be part of a personal computer, a workstation or any other computing device. The processor 402 may include cooperative operation of one or more general processors, digital signal processors (DSPs), application specific integrated circuits (ASICs), field programmable gate arrays (FPGA), digital circuits, analog circuits, and/or combinations thereof, and/or other now known or later developed devices for analyzing and processing data. The processor 402 may implement a software program, such as code generated manually or programmed. The processor 402 may operate and control at least a portion of the antifungal treatment system 100.

The processor 402 may communicate with the modules in the antifungal treatment system 100 via a communication path, such as a communication bus 408. The communication bus 408 may be hardwired, may be a network, and/or may be any number of buses capable of transporting data and commands. The modules and the processor may communicate with each other on the communication bus 408.

The memory system 404 may include a main memory, a static memory, and/or a dynamic memory. The memory 404 may include, but is not limited to computer readable storage media, or machine readable media, such as various types of non-transitory volatile and non-volatile storage media, which is not a signal propagated in a wire, including but not limited to random access memory, read-only memory, programmable read-only memory, electrically programmable read-only memory, electrically erasable read-only memory, flash memory, magnetic tape or disk, optical media and the like. In one example, the memory 404 includes a cache or random access memory for the processor 402. In addition or alternatively, the memory 404 may be separate from the processor 402, such as a separate cache memory of a processor, the system memory, or other memory. The memory 404 may also include (or be) an external storage device or database for storing data. Examples include a hard drive, compact disc ("CD"), digital video disc ("DVD"), memory card, memory stick, floppy disc, universal serial bus ("USB") memory device, or any other device operative to store data.

The memory 404 is operable to store instructions executable by the processor 402 and data. The functions, acts or tasks illustrated in the figures or described may be performed by the programmed processor 402 executing the instructions stored in the memory 404. The functions, acts or tasks may be independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

The antifungal treatment system 100 may also include a signal processing module to receive and process input signals and generate output signals. The signal processing module may include analog-to-digital (A/D) converters, Digital-to-analog (D/A) converters, gain amplifiers, filters and/or any other signal processing mechanisms, devices and/or techniques. Input and output signals may be analog signals, digital signals, or some combination of analog and digital signals.

In addition, or alternatively, the antifungal treatment system 100 may include a network module, which may provide an interface to a network. Data and commands may be communicated by the network module over the network. The network module may include a communication port that may be a part of the processor 402 or may be a separate component. The communication port may be created in software or may be a physical connection in hardware. The connection with the network may be a physical connection, such as a wired Ethernet connection, or may be established wirelessly. The network may include wired networks, wireless networks, Ethernet AVB networks, or combinations thereof. The wireless network may be a cellular telephone network, an 802.11, 802.16, 802.20, 802.1Q or WiMax network. Further, the network may be a public network, such as the Internet, a private network, such as an intranet, or combinations thereof, and may utilize a variety of networking protocols now available or later developed including, but not limited to TCP/IP based networking protocols.

Figure 5:
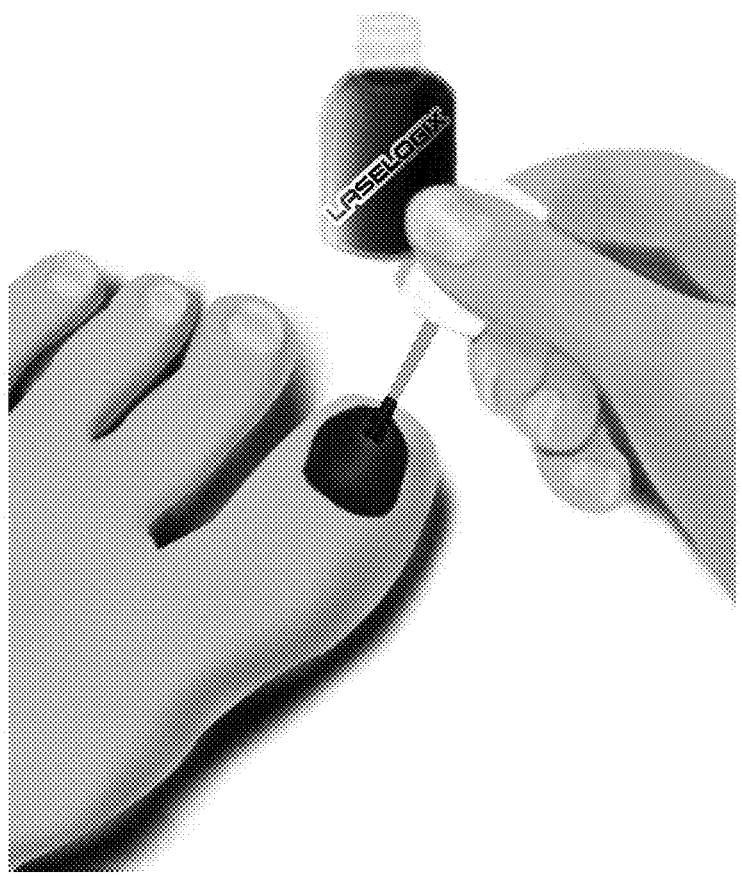
FIG. 5 is an example of how a user might apply the temperature sensitive liquid-bandage.

FIG. 5 is an example illustration of a liquid bandage. One difficulty in curing fungus associated with human nails such as toenails is that toenails grow very slowly, and because of this, they are constantly re-infected during the duration of the treatment process, which significantly negates the effect of the treatment. For this reason, the antifungal treatment system 100 may be used, not only to kill toenail fungus, but to also create and cure an "adhesive liquid bandage." This adhesive bandage may be infused by the system with an anti-fungal agent to create an anti-fungal "liquid bandage", which is cured and hardened to stay in place for extended periods of time while the initial treatment is happening. This bandage may seal the area under the toenail where fungus can enter, stopping re-infection. The bandage may also have anti-bacterial and anti-fungal properties. Further, the bandage can have a sealing effect to block transmission of light and oxygen to the area. The bandage can include a temperature-sensitive dye which will allow the user to see the non-visible or visible electromagnetic source treating an area. The dye could resemble nail polish. In one example, when the light source is emitting light onto the polish, the polish can change color at a particular temperature, anywhere in the range of 89 to 150 degrees Fahrenheit.

In addition to a bandage, the system may also apply any other form or topical solution to the infected area of the user. In one example, the solution may be a medication, such as an over the counter or a prescription medication. In another example, the solution may be a pretreatment solution, such as a solution to optimize penetration and effectiveness of the treatment energy. The application may be automated, and may include mechanical aspects, such as a brush, high pressure spray, and/or any other mechanism to apply a solution to the area.

The system may also provide automated capability to immerse the area in a solution for a predetermined period of time. In this example, the area to be treated may be enclosed in a cavity included in the system, which may then be partially or completely filled with a solution. The solution may remain in the cavity and then be automatically removed as part of a cycle of the system. Alternatively, or in addition, the application of solutions to the area may be manually initiated and/or manually ended by the user using the user interface.

Referring again to FIG. 4, where the light source 102 is electrically powered, the system may optionally include a power supply 410. The power supply may be an AC or a DC power supply, and may include an energy storage device, such as a battery or a capacitor. The processor may be a microprocessor, a logic array, or any other mechanism or device capable of providing the functionality of the device. In one example, the processor is capable of executing computer code, or instructions stored in memory to control the functionality of the system, including the power supply 410. The system may also include a user interface, such as push-buttons, a display, a touch-panel display, indicators, or some combination thereof, as previously discussed, which may be used to directly or indirectly control the power supply 410. The antifungal treatment system may be in the form of a battery powered clip-on toenail fungus killing system treating not only the infected toenail, but also curing the "liquid bandage".

The antifungal treatment system 100 may be in the form of a hand-held antifungal treatment system, with battery power and/or an AC power, or AC power adapter to DC. The system could use a microprocessor as well as a battery or AC adapter to power the device. The system can either be internally battery operated, or externally powered by using a battery pack that could strap onto the users body, for example, depending on the power needs. Alternatively, or in addition, the system may be operated with AC power, such as 120VAC.

In addition, the system may include a communication transceiver capable of sending and receiving information, as previously discussed. The communication transceiver may communicate using short range communication protocols, such as WiFi, Bluetooth, XBee, or Firewire, long range communication protocols such as CDMA, or 3G and/or network protocols such as TCP/IP communicating over wireless and/or wire-line communication paths. Thus, in some examples, the system may be controlled with a user interface presented on another device, such as a mobile device that is in communication with the system. In addition, transmission of data from a hand held device included in the anti-fungal treatment system may be used by another device such as a computer or mobile communication device to maintain treatment records, formulate a treatment plan, advise a treating physician of the status, provide alerts and reminders to the user, or any other aspects related to the user's treatment. Also, transmission of data to the hand-held device included in the anti-fungal treatment system may include download of operational instructions and/or parameters to customize the treatment related operation of the anti-fungal system. In addition, control of operation of the hand held device may be provided. Thus, in some examples, the processing capability and user interface of the anti-fungal treatment may be minimized.

FIG. 6 is an example of the antifungal treatment system Graphical User Interface, which may be included in the hand held device, such as the control panel 124, or provided on a separate device. The Graphical User Interface (GUI) can be used to control and develop treatment of the nail. For example, the user can interact with the GUI to take a picture to document their current fungal status, instruct the user to paint their nails with the temperature-sensitive liquid bandage, instruct the user how to use the light source, allow the user to apply the concentrated beam to their nail, allow the user to save their data on a particular treatment, or any other user related activities and/or interaction, which allows a user to interact with the system accurately and efficiently. The controller can save the data for the particular treatment, including but not limited to the picture taken by the camera, the total usage time of the treatment, the date and time of the treatment, the treatment number, and any other data which could assist the user in managing their treatment, which may include visually seeing their treatment produce results.

Figure 7:
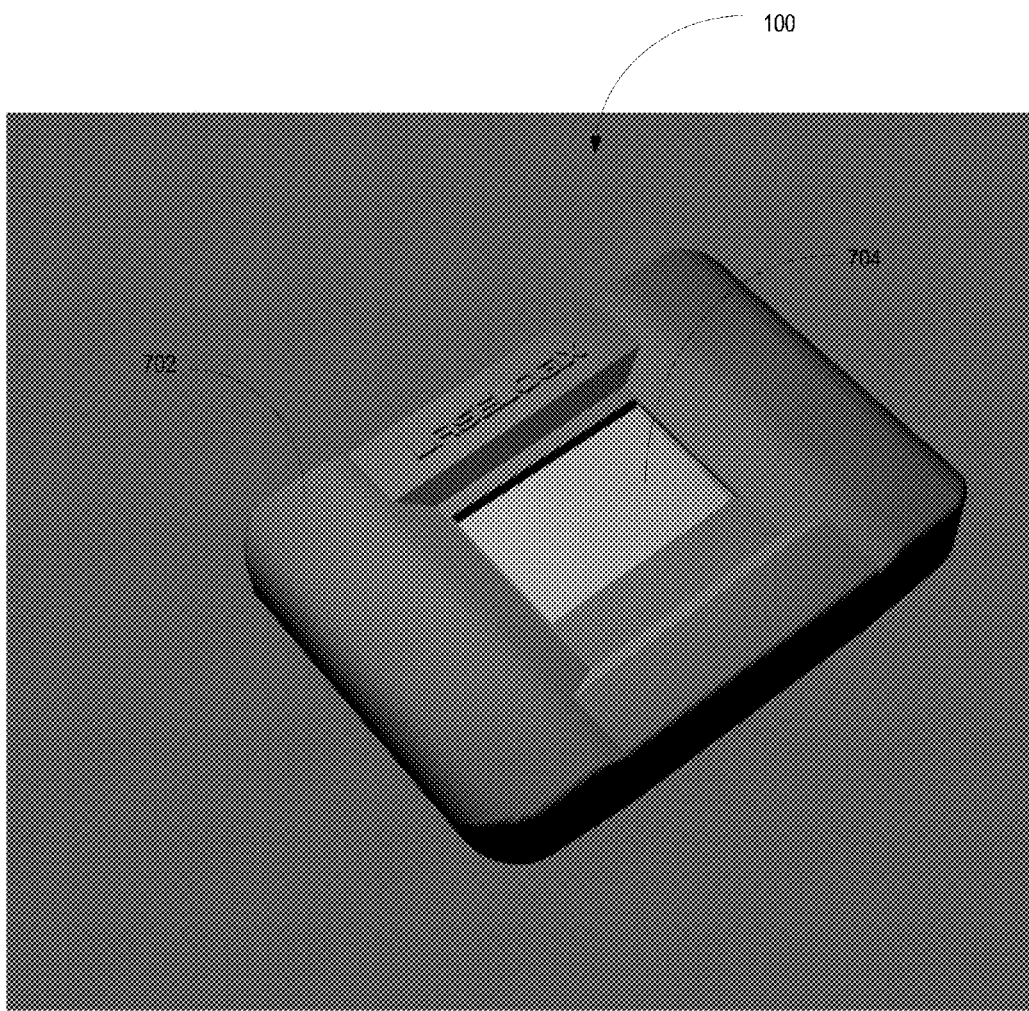
FIG. 7 is a perspective view of a housing of an example of the antifungal treatment system.
Figure 8:
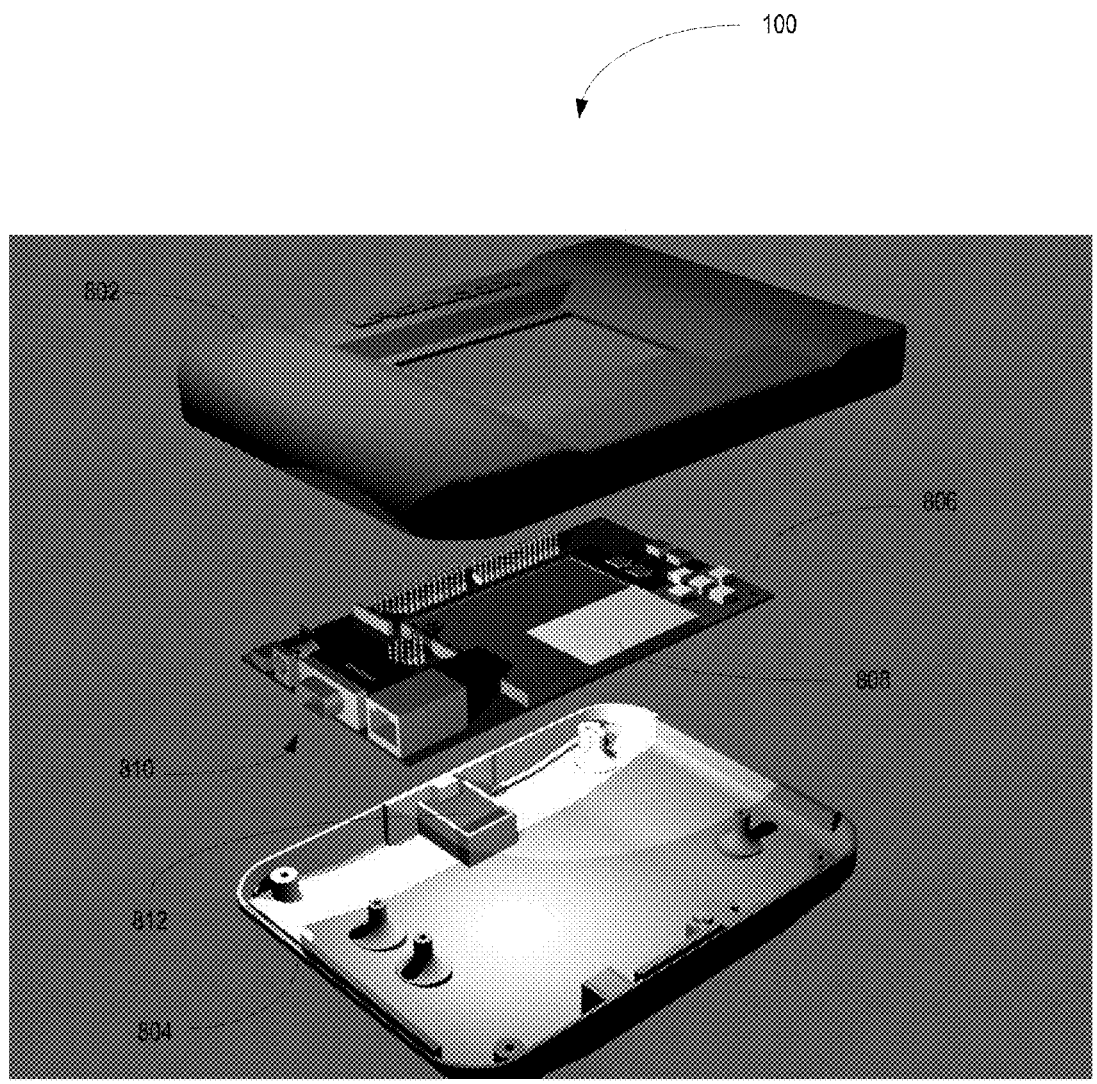
FIG. 8 is a perspective exploded view of an example of the antifungal treatment system.

FIG. 7-10 describe another example of the antifungal treatment system 100. FIG. 7 illustrates a perspective view of a housing 702 that includes a display 704. FIG. 8 is an exploded perspective view of the antifungal treatment system 100 of FIG. 7 illustrating that the housing 702 is a multi-piece housing having a top piece 802 and a bottom piece 804. Included in the housing is the light source, the processor, the memory system, and/or the sensing device, which may be positioned in the cavity formed with the top and bottom pieces 802 and 804. In the example of FIG. 8, some of the components of the antifungal treatment system 100 are included on one or more circuit boards 806 mounted in the housing 702. Also depicted in FIG. 8 are an example display 808, an example input/output interface 810 included on the circuit board 806. A light source module 812 is illustrated as mounted on the bottom piece 804 of the housing 702. The light source module 812 may include a light source 102, such as a laser, and a sensing device 406, such as a camera.

Figure 9:
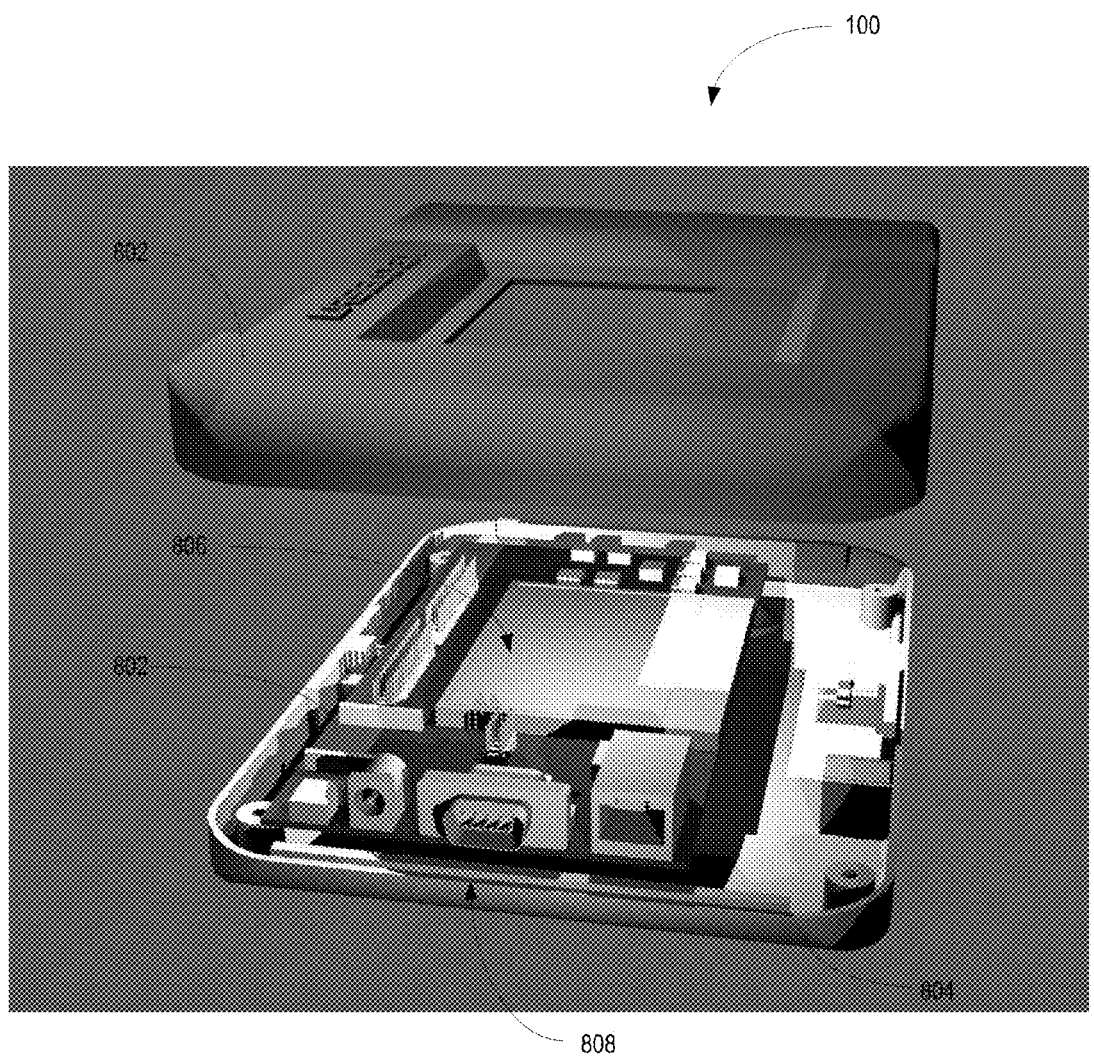
FIG. 9 is another perspective of an example of the antifungal treatment system.
Figure 10:
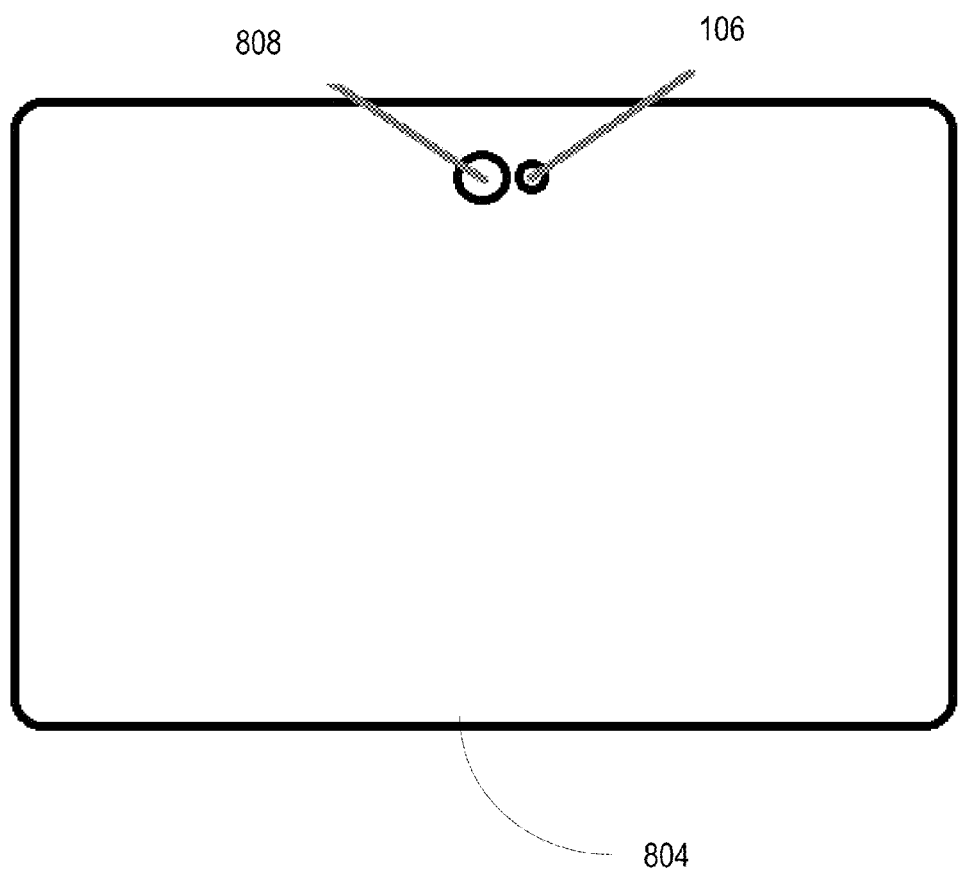
FIG. 10 is a diagram of a housing, a light source and sensing device in an antifungal treatment system.

FIG. 9 is another exploded perspective view of the antifungal treatment system 100. In FIG. 9, the circuit board 806 is mounted in the cavity within the bottom piece 804 of the housing 702, such that the display 806 is aligned with an aperture formed in the top piece 802 of the housing 702, and the input/output interface 810 is positioned along an edge of the bottom piece 804 of the housing 702. FIG. 10 is a perspective view of a surface of the bottom piece 804 of the housing 702 opposite the circuit board 806. The bottom piece 804 of the housing 702 may include the exit aperture 106 configured to allow a concentrated beam of electromagnetic radiation to exit the housing 702, as previously discussed, and a sensing aperture 1002. The sensing aperture 1002 may allow a sensing device, such as a camera, access to the target area where the focal point of the concentrated beam is position. In other example, the sensing device may be a temperature probe, a light sensor, or any other form of sensing device. The camera may include the ability to detect light in the visible as well as infrared region, which is normally invisible to the human eye. Accordingly, a user of the system may use the camera to see the position of the invisible infrared energy by viewing an image generated by the camera. The image may be provided on a separate display, or on an image display included in the housing.

Example Methods and Testing

Although particular test methods and examples are described below using a laser, the antifungal treatment system should not be construed as limited in this regard. Instead, it should be understood that the operation of the portable system is flexible and various parameters and procedures are readily changeable to accommodate different treatment plans, light sources, and cells or fungus.

Assessment of Laser Effects in *S. cerevisiae*

To determine the amount of energy needed from a 1064 nm laser to achieve a decreased viability of a cells, such as *Saccharomyces cervisiae* (Sigma-Aldrich, St. Louis, Mo., USA) cells were lased and grown in rich media. *S. cervisiae* was grown aerobically in YPD at 30° C. in a shaking water bath overnight. Cells were standardized to OD600 0.8, all optical density was performed by taking 100 µL of cells and adding it to 900 µL water in a cuvette tube. 100 µL of cells was placed in a sterile 96 well plate and lased at 5 cm distance with the laser set to 1 Hz 75% duty cycle. At 0, 20, 40, 60, and 90 minutes 3 µL of cells were removed and used to inoculate 3 mL YPD culture in 15 mL test tube: performed in triplicate. Yeast cells were allowed to grow at room temperature for 24 hours. Cell growth was determined using optical spectroscopy (Model USB4000 UV-VIS spectrometer and Spect-ra-Suite software, Ocean Optics, Dunedin, Fla.) connected to a laptop computer to determine OD600.

Figure 11:
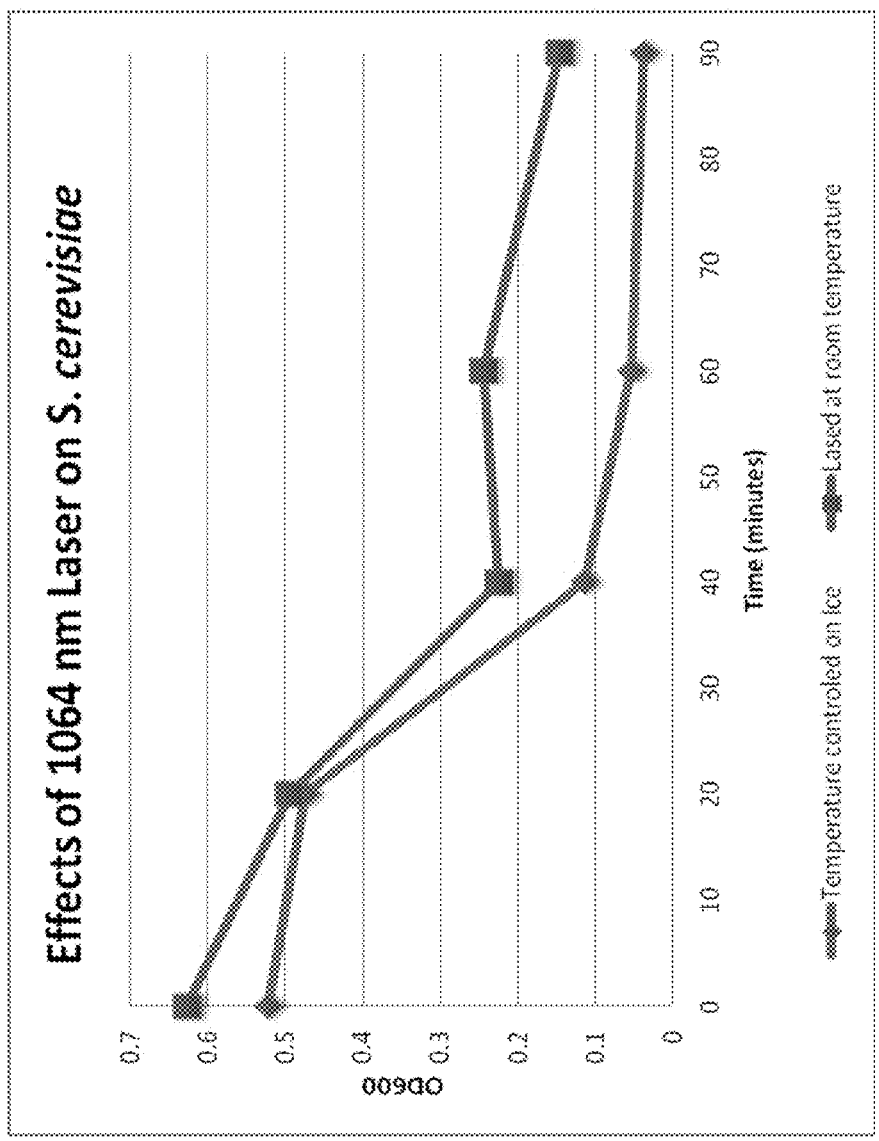
FIG. 11 is experimental results of fungus eradication with the antifungal treatment system.

FIG. 11 is an example of decreased cell viability from laser exposure. In FIG. 11, *S. cerevisiae* was lased (1 Hz, 75% duty cycle) with a 1064 nm laser for varying times to determine how the laser impacted the number of colony forming cells. Cells were lased on Ice or at room temperature. The cell lased at room temperature never reached a temperature above 25° C. The cells lased on ice were all kept on ice for a total time of 90 minutes.

Assessment of Effects on *Trichophyton ruburm*

*T. rubrum* was by grown by inoculating 200 µL of LB a in a 96 well plate with 100 µL of viable cell solution. The fungus was grown at 28° C. for 7 days or until the fungus filled 70% of the well. Cell solution was prepared by placing 3 wells of fungus from a 96 well plate in 3 mL of LB in a test tube. Borosilicate glass beads were added and the solution was vortexed using a VWR digital vortex set at 3000 rpms in short pulses until the large clumps of cells were gone. 100 µL of cells was placed in 0.5 mL tube and lased at 5 cm. When lased 12 µL of cells was removed at varying times and plated on sabouraud dextrose plates as four 3 µL drops. If the cells were lased on ice the same protocol was used as described as above, all cells were on ice for a total time of 90 minutes. Cells were allowed to grow until control colonies were developed.

Figure 12:
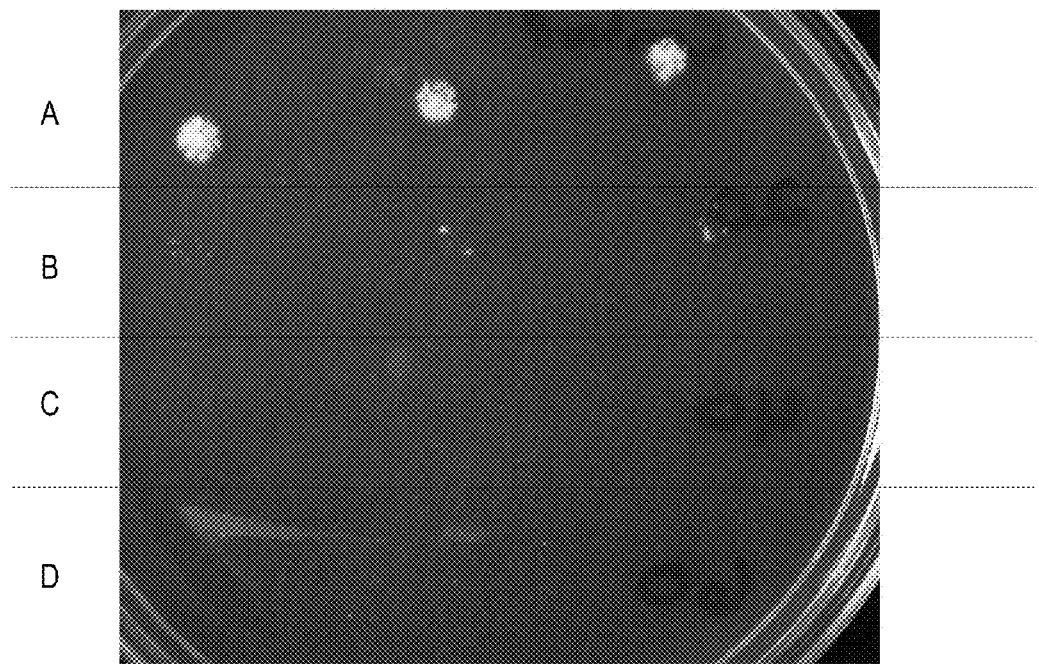
FIG. 12 is additional experimental results of fungus eradication with the antifungal treatment system.

FIG. 12 is an example of the effects of 1064 nm Laser on *T. rubrum*. In FIG. 12, the area indicated as "A" is the control area and illustrated untreated *T. rubrum*. Area "B" indicates the condition of the *T. rubrum* after 20 minutes of exposure to the electromagnetic radiation from the laser. Area "C" indicates the condition of the *T. rubrum* after 40 minutes of exposure to the electromagnetic radiation from the laser. Area "D" indicates the condition of the *T. rubrum* after 60 minutes of exposure to the electromagnetic radiation from the laser. In FIG. 12 an example of 100 µL of *T. rubrum* solution was lased (1 Hz, 75% duty cycle) in 96 well plate. Three 3 µL aliquots were removed at 0, 20, 40, 60 and plated in a row on the agar.

MDH Assay

Cells were standardized as described as above for *T. ruburm* or *S. cerevisiae* and either lased or use as a control. First, 100 µL of cell's were placed in a 1.7 mL eppendorf tube and spun on a tabletop microfuge at top speed for 5 minutes. Cells were then suspended in 100 µL of lysis buffer (1 mM DDT, 100 mM KCl, 1 mM EDTA). Homogenized took place by adding 5 3 mm glass beads to cells then vortexing at 3000 rpm for 30 seconds followed by 30 seconds of icing, six cycles of vortexing and ice took place. Glass beads were then removed and the solution was spun on a tabletop centrifuge at top speed for five minutes to pellet nonsoluble proteins. The supernatant containing the MDH was then placed in a clean tube on ice. The reaction was initiated by adding 70 μL of supernatant to 1 mL of reaction mix (10 mM malate, 10 mM glutamic acid, 1 mM NAD, Glutamic oxaloacetic transaminase, and 0.05% BSA pH 8.0) and was monitored via spectroscopy (Model USB4000FL spectrometer and SpectraSuite software, Ocean Optics, Dunedin, Fla.) connected to a laptop computer at 340 nm to detect the formation of NADH.

Figure 13:
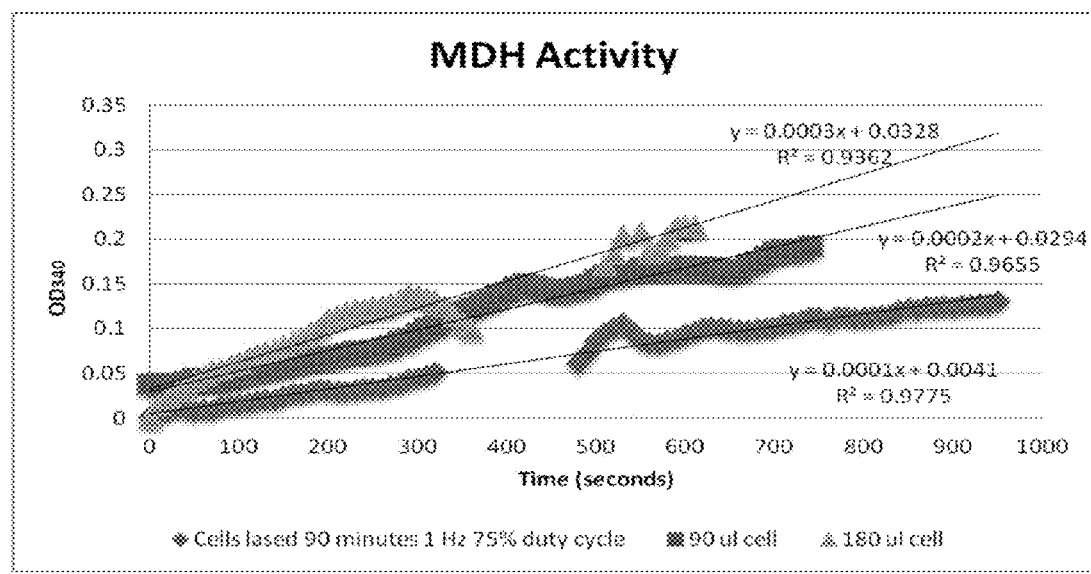
FIG. 13 is additional experimental results of fungus eradication with the antifungal treatment system.

Decreased MDH activity in lased *S. cerevisiae* is illustrated in FIG. 13.

Activity of MDH isolated from *S. cerevisiae* using the procedures described in FIG. 13. Both lased cells and 90 μL cells represent the same cell density. 180 μL of cells is represent that reactants are not rate limiting.

The data shows electromagnetic radiation generated by the 1064 nm laser is triggering a cellular event leading to cell death in *S. cervisiae* that may not be entirely from a heating effect. When the cells were lased in a cuvette exposed to an open atmosphere the temperature never exceeded 25° C., the temperature must be in excess of 40° C. for over 60 minutes before heat can cause cell death. When the cells were lased on ice the temperature was controlled at 4° C. When compared to control a decreased viability of the cells could be found when they were lased on ice or at room temperature. This experiment shows that the event-taking place leading to the death of *S. cervisiae* may not be fully dependent on heat. (FIG. 11)

When *T. rubrum* was lased the same effect is taking place as seen in the yeast, as the time exposed to the laser increase there is a decreased viability of the cells. The major difference between the result from the yeast and the *T. rubrum* is with the toenail fungus the time of laser irradiation can be much shorter before a decrease in the cells viability can be detected. With the toenail fungus after 20 minutes of exposure to the laser almost complete cell death was achieved, with the yeast it took 40 minutes of laser irradiation before decreased cell viability can be calculated. (FIG. 12)

To study if intracellular protein damage is taking place an enzymatic assay of Malic dehydrogenase was performed. MDH was chosen due it being present both in the mitochondria and cytosol. When MDH was extracted from *S. cervisiae* that was lased for 90 minutes and compared to control *S. cervisiae* at the same density the cells that were lased showed a decreased activity of the MDH. The decreased activity of MDH can be attributed to some type of nonspecific protein damage that is not caused by a heating effect.

Reactive oxygen species are a probable cause of the decreases viability for several reasons. First, photons coming from the 1064 laser are not energetic enough to break the peptide bond causing a protein to become denatured. Second, the temperature when the cells were being lased never exceeded 25° C., in order to cause the cells to be damaged by heat the temperature may have to be above 40° C. (data not included). It may be possible for a 1064 photon to change the tertiary structure by way of modifications sites by protonation, phosphorylation, or ubiquitination site. It has been shown that a 870 nm laser absorbs at cytochrome aa3 generating ROS. Our data shows that when cells are exposed to the laser there is a time dependent effect supporting the reactive oxygen species hypothesis. ROS is a likely candidate because both 870 and 1064 are near infrared wavelengths and have similar characteristics.

In addition, the system may be configured to provide the modulated light energy at a lower power and over longer period of time than a laser. The net effect is a low cost, portable system which has the effectiveness of a laser treatment, but negates the need to visit a doctor's office.

During operation, the system may selectively energize and de-energize the electromagnetic light source(s) in a predetermined sequence. The predetermined sequence may be fully automated. Automation of the sequence may be by timers, a processor, or any other mechanism or device, as previously discussed. In addition, the intensity of the light source(s) may be varied. In one example, a first and second light source may be energized at substantially the same time to treat the affected area. The first and second light sources may be fixed, or movable. In one example, the first and second light sources may be movable to be positioned in a location to optimize exposure of the part of the user in the target area to the light energy being emitted by the first and/or second light sources. The intensity of the sources may also be varied. The pulse duration of the sources may also be varied.

In addition to automated control of the electromagnetic light source, the system may also perform automated mechanical processing of the area. Such mechanical processing may involve the removal of dead skin and other material by brushes, high pressure spray or any other removal mechanism. In one example, trimming, such as toenail trimming to eliminate the infection may also be performed by the system. Such trimming may be completed with cutters, burrs, sanders, or any other mechanism for removing toenail material. In addition, grinding and sanding of the surface(s) of the nail may also be performed in an automated fashion with the system. Alternatively, or in addition, a user may manually initiate, or manually terminate any mechanical processing by the system. Manual control during any mechanical processing may also be performed by the user.

The system could be a hand held, ergonomic device. This device could then be used to aim the electromagnetic source light to a particular location on the nail. Using this method, the user could pinpoint the location as to where the fungus should be killed. Alternatively, or in addition, the electromagnetic lights sources may swivel or pivot, manually and/or automatically to be pointed to a desired location.

Observations and Further Analysis

Nail Fungus, which may commonly be *Trichophyton rubrum*, is a complex organism and not as well documented as yeast. There is little to no studies on the stress pathways in *T. rubrum*, opposed to yeast, which has a documented genome sequenced and stress pathways. Using a yeast model can allow for testing mutants with key protein knockouts of reactive oxygen species scavengers, oxidative stress, heat shock, DNA damage repair, osmolarity balance, redox state of the cell, and cell check points.

Continue light source tests on the well known yeast (*Saccharomyces cervisiae*) and following the yeast stressor pathways may provide a determination of the exact cause of yeast death from the light source.

Once the visible light from the light source enters a human cell (in our case yeast and fungus), the light is converted to vibration; the vibration to heat. The light itself may contribute to the cell cause of death. Detection of reactive oxygen species, and detection of precise stressor pathways in yeast, can be used to confirm how proteins become denatured, or DNA altered, or cell wall ruptured, or other causes of death of the cell.

The cause of death in yeast may be used to predict the cause of death in fungus (*T. rubrum*). Using the yeast model, pathways that are hypersensitive to being subject to a light source, such as being lased at 1064 nm may be identified. The identified pathways may be applied to specific assays on *T. rubrum* to validate that the laser is killing the cell via the same mechanism. A yeast model may be used because it allows a high throughput approach to test many different, well known cellular stress ways.

Where the correct stressor pathway(s) in yeast is identified, and the same event occurs in fungus upon application of laser light, then the related subject stressor pathway(s) chromophore (color) in fungus can be targeted by selecting the opposite laser light color for maximum energy absorption. This can allow the laser to operate at the absolute minimum power level for safety, and target only the precise chromophore of interest to minimize collateral tissue damage (i.e it will kill the fungus however there will be only very slight pain to the user, and literally no collateral skin or tissue damage. The product can also be used as often as desired as there are no known detrimental effects, which may be present with UV light).

Selection of the wavelengths of the laser diodes may be based on an optimum wavelength for kill, and the minimum power needed. As a result, a laser diode of the optimum power and wavelength may be used to make the device safe and low cost.

Light affects living organisms in many ways that we do not understand. We can use "light" to kill our toenail fungus. It is hypothesized by many physicists and philosophers that people, animals and others creatures evolved over time to be able to "see" light (i.e. the visible portion of the electromagnetic spectrum) because of the following . . . "what a great survival advantage a creature would have if it could "see". Human eyes have a very unique quality in that they can perceive the frequency of the electromagnetic spectrum we call the "light frequency". There are many frequencies of the electromagnetic spectrum which humans cannot "see." Light is merely electromagnetic radiation that human eyes can "see." Light perceived by humans, for example, includes electromagnetic radiation incident on the earth's surface from the sun.

Light includes properties useful for killing toenail fungus that lives beneath the nail of a human. Simply put, light has the ability to penetrate a top surface of the nail (i.e. shine through the top surface and a bottom surface of the nail) to get to the skin below the nail (i.e. where the fungus lives on the bottom surface of the nail) and it can "shine through" without damaging the nail. This is unique to electromagnetic radiation and has advantages over pills or topical crèmes. Light can "get to" the problem fungus area very quickly, whether from a man-made light source, such as a laser or the sun, or any other light source. The portion of light we are "primarily" concerned with is infrared radiation. Infrared radiation (light) generates heat. Infrared radiation can pass through the nail without damaging the nail, and then heat the fungus to the point that it is "shocked" and dies. Many other wavelengths of electromagnetic radiation could also kill toenail fungus (such as electromagnetic radiation in the non-visible spectrum).

Light sources that use solar energy such as the sun may be used to kill toenail fungus. In addition to being less expensive generation of electromagnetic radiation from external light sources such as the sun are effective in killing the toenail fungus. Light sources using electrical power, such as a laser may also be used. Light sources such as lasers may be used in the infrared region. The laser generates a man-made collimated light of a predetermined specified frequency. Lasers operating at such a predetermined frequency can penetrate a top surface of the nail and a bottom surface of the nail and kill toenail fungus on the bottom surface, however, in some examples the concentrated light from an external light source, such as the sun may work faster and better. By generating electromagnetic radiation as a concentrated beam from solar energy, all the wavelengths of the external energy source may be directed toward the fungus, not just the specific laser frequency. This may result in a more effective kill of the fungus due to the combination of all the frequencies of "white light" (or visible light) included in the external light source being more effective in killing fungus than the laser's single frequency. In some examples, a filter, such as a ultraviolet light (UV) filter, may be used so that the UV portion of the spectrum is eliminated. In other examples, the UV component can be included as part of the electromagnetic radiation generated by the system. Other frequencies of the visible white light may also include preferential properties for either killing the fungus, or healing human skin tissue. Thus, fFocused, concentrated visible light from any source, thru any combination of mirrors, lasers, lenses, light pipes, special high intensity bulbs, etc. can be effective in killing toenail fungus. In addition, any source of visible light that emits infrared radiation which creates heat below the nail can kill fungus Example operation with the system described herein may occur about once per month. This gives the human body time to heal between applications. When using the system, the concentrated beam of light should be directed such that a fine point of light is focused on the target area, such as a nail. This focused point light should be maintained on the target area until a predetermined temperature of the target area is reached, such as about 40 to 43 degrees Celsius, at which point the target area should be moved to the next area to be treated and the procedure repeated. The idea is to treat the affected area once/month until nails are cured. The power intensity in the target area can be adjusted by holding the system closer/farther from the nail to increase/decrease the "power." Alternatively, the alignment tool may be used to adjust/maintain the power intensity. Each part of the infected nail should be used as the target area during each treatment even if areas look unaffected by the fungus. These seemingly unaffected areas may be where fungus is living, but just can't be seen.

While various embodiments of the invention have been described, it will be apparent to those of ordinary skill in the art that many more embodiments and implementations are possible within the scope of the invention. Accordingly, the invention is not to be restricted.

We claim:
1. A method of treating a fungus, the method comprising:
positioning a housing that includes a convex lens so that a longitudinal axis of the housing is oriented to be within a predetermined area defined as frusto-conical;
producing a concentrated beam of electromagnetic radiation with the convex lens in response to the positioning of the housing, the electromagnetic radiation being visible electromagnetic radiation and infrared electromagnetic radiation;
defining with an alignment tool a target area that is spaced away from the housing, the alignment tool comprising a proximate end coupled with the housing, and a distal end forming an alignment aperture, the target area defined by the alignment aperture to be a focal point of the concentrated beam of electromagnetic radiation;
directing the concentrated beam out of the housing to the focal point of convex lens, which is at the target area;
penetrating a human nail with the concentrated beam, the human nail positioned with the alignment tool to be in the target area; and
killing a fungus positioned behind the human nail with the concentrated beam.

2. The method of claim 1, further comprising subjecting the convex lens to an external light source.

3. The method of claim 2, wherein subjecting the convex lens comprises manipulating the housing so that solar energy from the external light source is incident on the convex lens, the solar energy from the external light source incident substantially perpendicular to a planar surface of the convex lens.

4. The method of claim 2, further comprising moving the convex lens from a first position to a second position, the convex lens moved to the second position so that solar energy from the external light source is incident on the convex lens, the solar energy from the external light source incident substantially perpendicular to a planar surface of the convex lens only when the convex lens is in the second position.

5. The method of claim 1, wherein positioning a convex lens comprises positioning the housing such that light energy from an external light source enters an entry aperture included in the housing.

6. An antifungal treatment system comprising:
a housing formed to include an entry aperture and an exit aperture;
a convex lens disposed in the housing and positioned to receive light energy received through the entry aperture when a longitudinal axis of the housing is aligned with the light energy;
the convex lens configured to produce a concentrated beam of visible light and infrared light from the light energy received at the entry aperture;
the convex lens further configured to direct the concentrated beam of light out of the housing through the exit aperture to a focal point of the convex lens located outside the housing; and
an alignment tool coupled with the housing and at least partially surrounding the exit aperture at a proximate end of the alignment tool, the alignment tool extending away from the housing to form an alignment aperture at a distal end of the alignment tool, the alignment aperture positioned to define a target area in which the focal point of the concentrated beam is located, and formed to align a human nail in the target area.

7. The antifungal treatment system of claim 6, further comprising a filter disposed in the housing, the filter configured to block ultraviolet frequencies of the visible light energy, and pass all other frequencies included in the light energy.

8. The antifungal treatment system of claim 6, further comprising a controller configured to control generation of the concentrated beam of light.

9. The antifungal treatment system of claim 6, further comprising a control panel positioned on the housing, the control panel configured to provide user control of the antifungal treatment system.

10. The antifungal treatment system of claim 9, wherein the control panel comprises a switch configured to be moved between a first position in which the convex lens is unable to receive the visible and infrared light energy and therefore unable to produce the concentrated beam of visible light and infrared light, and a second position in which the visible and infrared light energy is received by the convex lens so that the convex lens produces the concentrated beam of visible light and infrared light.

11. The antifungal treatment system of claim 6, further comprising a processor configured to monitor and control operation of the antifungal treatment system.

12. An antifungal treatment system comprising:
a housing having a longitudinal axis;
a convex lens disposed in the housing, the convex lens operable to produce visible electromagnetic radiation and infrared electromagnetic radiation only when the longitudinal axis of the housing is aligned substantially vertically so as to remain within a predetermined area;
the electromagnetic radiation being in a concentrated beam provided at a focal point of the convex lens in a target area located external to the housing; and
an alignment tool comprising a first end coupled with the housing and a second end extended away from the housing, the second end defining the target area in which the focal point of the convex lens is located, and the second end defining a position for a human nail to be in the target area at the focal point.

13. The antifungal treatment system of claim 12, wherein the convex lens is operable to produce the electromagnetic radiation when energized with an external light source.

14. The antifungal treatment system of claim 13, wherein the external light source is the sun.

15. The antifungal treatment system of claim 13, further comprising a filter disposed in the housing, the filter operable to filter ultraviolet light provided by the external light source so that the ultraviolet light is excluded from the electromagnetic radiation produced with the convex lens.

16. The antifungal treatment system of claim 12, further comprising a DC power supply included in the housing to power the antifungal treatment system.

17. The antifungal treatment system of claim 12, further comprising a battery included in the housing to power the antifungal treatment system.

18. The antifungal treatment system of claim 12, further comprising a timer configured to time a length of exposure of the human nail to the concentrated beam while the human nail is positioned with the alignment tool in the target area at the focal point.

19. The antifungal treatment system of claim 6, wherein the alignment tool comprises a shroud coupled with the alignment tool proximate the distal end, the shroud being a translucent material.

\* \* \* \* \*